United States Patent [19]

Kruper, Jr.

[11] Patent Number: 4,668,832
[45] Date of Patent: May 26, 1987

[54] DEHYDRATION OF HALOGENATED, UNSATURATED ALCOHOLS TO FORM HALOGENATED, CONJUGATED DIENES

[75] Inventor: William J. Kruper, Jr., Sanford, Mich.

[73] Assignee: The Dow Chemical Company, Midland, Mich.

[21] Appl. No.: 785,636

[22] Filed: Oct. 8, 1985

[51] Int. Cl.[4] ............................................. C07C 17/00
[52] U.S. Cl. ..................................... 570/142; 570/143; 570/153; 570/190; 570/193; 570/217
[58] Field of Search ............... 570/142, 143, 190, 193, 570/217, 153

[56] References Cited

U.S. PATENT DOCUMENTS

| | | | |
|---|---|---|---|
| Re. 31,330 | 8/1983 | Fujita et al. | 570/142 |
| 3,483,263 | 12/1969 | Schlichting et al. | 570/217 |
| 3,689,580 | 9/1972 | Hall et al. | |
| 4,078,008 | 3/1978 | Lantsch et al. | 570/142 |
| 4,081,488 | 3/1978 | Scharpf | 570/217 |
| 4,191,712 | 3/1980 | Arlt et al. | |
| 4,216,173 | 8/1980 | Kysela et al. | 570/217 |

Primary Examiner—Natalie Trousof
Assistant Examiner—Joseph A. Boska
Attorney, Agent, or Firm—Jerri L. Jazbinschek

[57] ABSTRACT

Halogenated, unsaturated alcohols are dehydrated by contacting the alcohol and a carrier gas with a silica alumina catalyst to form dienes of the formula:

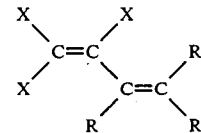

wherein each X is independently hydrogen, fluorine chlorine, or bromine with the proviso that no more than one of them is hydrogen, and each R is independently hydrogen, alkyl, aralkyl, alkaryl, or aryl.

17 Claims, No Drawings

DEHYDRATION OF HALOGENATED, UNSATURATED ALCOHOLS TO FORM HALOGENATED, CONJUGATED DIENES

BACKGROUND OF THE INVENTION

This invention relates to the dehydration of halogenated unsaturated alcohols to form the corresponding halogenated conjugated dienes.

The dehydration of unsaturated alcohols to form conjugated dienes is well-known. However, reaction conditions which give good results with non-halogenated unsaturated alcohols, when used with halogenated unsaturated alcohols, can allow polymerization, isomerization, rearrangements, and other undesired side reactions. These reactions compete with the production of the halogenated diene and thus cause low yields and an impure product.

It is known to dehydrate nonhalogenated unsaturated alcohols by contacting them, in the vapor phase, with a catalyst in the presence of steam. See, e.g., U.S. Pat. Nos. 3,657,376 and 4,049,736.

U.S. Pat. No. 4,078,008 discloses the formation of 1,1-dichloro-4-methyl-1,3-pentadiene in yields of up to 88 percent by the dehydration of 1,1-dichloro-4-hydroxy-4-methyl-1-pentene. All examples show liquid phase reactions.

U.S. Pat. Nos. 4,081,488 and 4,216,173 disclose the dehydration of 1,1-dichloro-3-hydroxy-4-methyl-1-pentene to form 1,1-dichloro-4-methyl-1,3-pentadiene in yields of up to 89 percent using dehydrating catalysts such as activated clay, aluminum oxide, and aluminum silicate. All examples show liquid phase reactions.

British Pat. No. 1,528,119 and British Pat. No. 1,554,690 disclose the gas phase dehydration of 1,1-dichloro-3-hydroxy-1-butene with an aluminum oxide catalyst to form 1,1-dichloro-1,3-butadiene in about 90 to 92 percent yield.

*Bull. Chem. Soc. Jap.*, Vol. 40, pp. 1991-2, (1967) discloses the liquid phase dehydration of 1,1,2-trichloro-3-hydroxy-1-butene to give yields of up to 51 percent of 1,1,2-trichloro-1,3-butadiene.

U.S. Pat. No. 3,483,263 discloses the gas phase dehydration of 1,1,2-trichloro-3-hydroxy-1-butene over activated alumina to form the diene in about 73 percent yield.

The prior art processes tend to require the use of an inordinate amount of catalyst. In many cases one part by weight of catalyst does not convert even one part by weight of alcohol. The prior art methods leave room for improvement in conversion, selectivity, yield, catalyst efficiency, or any combination of these. Thus, it would be highly desirable to possess a process for the production of halogenated conjugated dienes, especially the highly reactive tri-halogenated dienes, which would provide some or all of the improvements listed above.

SUMMARY OF THE INVENTION

The present invention is such a method of preparing halogenated conjugated dienes in high yield and purity. According to the method of the present invention, halogenated conjugated dienes, as hereinafter described, are produced by contacting a halogenated unsaturated alcohol with a silica alumina catalyst in the presence of a carrier gas under the proper reaction conditions. Surprisingly, the method of the present invention produces the dienes of the invention in high yield and purity. Use of the present invention reduces the occurrence of competing reactions, such as rearrangement and polymerization, especially with the more reactive tri-halogenated compounds. This reduction of side reactions combined with the high conversion rate of the alcohol account for the high yield and purity of the product. Since no organic solvents are used, purification is simplified and there is less waste material for disposal. An additional advantage of the method of the present invention over the prior art methods is that the instant method makes efficient use of the catalyst in that the catalyst can dehydrate several times its weight in alcohol before regeneration is needed. The products of the method of the pesent invention are useful in several applications, including their use as precursors to adhesives, polymers, insecticides, and latexes.

DETAILED DESCRIPTION OF THE INVENTION

Generally, the preferred halogenated unsaturated alcohols employed in this invention are represented by formula I:

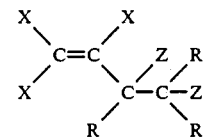

wherein each X is independently hydrogen, fluorine, chlorine, or bromine, with the proviso that no more than one of them is hydrogen. Each R is independently hydrogen, alkyl, aralkyl, alkaryl, or aryl. One Z is hydrogen and the other Z is hydroxy. For the purposes of this invention, alkyl includes cycloalkyl groups and straight- or branched-chain alkyl groups with substituents limited to those which will not interfere with the dehydration reaction. Preferably, each is independently hydrogen, alkyl, alkaryl, aralkyl, or aryl wherein each R has up to about 10 carbon atoms. More preferably, each R is independently hydrogen or lower alkyl with up to about 8 carbon atoms. Preferably, each X is independently fluorine, chlorine, or bromine. More preferably, each X is independently chlorine or bromine. Most preferably, each X is chlorine.

The halogenated unsaturated alcohol starting material can be made by any suitable method. Some of the methods known in the art for the synthesis of these alcohols are disclosed in *Bull. Chem Soc. Jap.*, Vol. 40, pp 1991-2, (1967); British Pat. No. 1,528,119; British Pat. No. 1,554,690; U.S. Pat. No. 3,483,263; U.S. Pat. No. 4,081,488; and U.S. Pat. No. 4,216,173, the teachings of which, with respect to these alcohols, are incorporated herein by reference.

The silica alumina catalyst typically comprises from about 10 to 100 percent silica ($SiO_2$) and from about 90 to 0 percent alumina ($Al_2O_3$). Preferably, the catalyst comprises from about 85 to about 90 percent silica and about 10 to about 15 percent alumina. Most preferably, the catalyst is about 87 percent silica and about 13 percent alumina. The surface area of the catalyst should be greater than about 350 $m^2/g$, but less than that surface area at which the catalyst would sinter at the reaction or regeneration temperatures. A preferred surface area is from about 400 $m^2/g$ to about 450 $m^2/g$. Catalysts having lower surface area are typically less active.

One part by weight of the catalyst typically converts more than about 5 parts by weight alcohol before regeneration is required. Preferably, one part by weight of the catalyst can convert more than about 6 parts by weight alcohol. Most preferably, one part by weight of the catalyst can convert more than about 7 parts by weight alcohol.

The catalyst can be regenerated by heating to a temperature above the reaction temperature while passing an oxygen-containing gas through the catalyst bed. A preferred regeneration temperature range is from about 500° C. to about 600° C. A more preferred range is from about 560° C. to about 580° C. The regeneration process can be repeated.

The carrier gas typically is an inert gas or a mixture of inert gases which does not interfere with the reaction. Preferably, the carrier gas comprises steam or more preferably a mixture of steam with at least one other inert gas. The steam serves as an effective carrier gas for the relatively nonvolatile alcohol, reducing its tendency to condense on the catalyst. Low water concentrations allow condensation of the organic phase on the catalyst bed which promotes coking. High water concentrations favor allylic rearrangement. Examples of the other inert gases which may be used as carrier gases include argon, helium, and nitrogen. This non-steam carrier gas is typically employed in amounts described as a mole ratio of carrier gas to alcohol ranging from 0.1:1 to 2:1. The amount of steam typically employed can conveniently be described as a weight ratio of water to alcohol. The weight ratio of water to alcohol in the feed stream typically is from about 0.1:1 to about 10:1. A preferred ratio is from about 0.5:1 to about 3:1, with the most preferred ratio being from about 1:1 to about 2:1.

The process can be conducted in a batch or continuous manner. The process is preferably conducted in a continuous manner by causing a vaporous mixture of alcohol and carrier gas to flow into contact with the catalyst under conditions which allow the dehydration to take place.

The process can be conducted at any combination of temperature and pressure at which the reaction will occur. The temperature range for conducting the reaction of the present invention typically varies from about 150° C. to about 500° C. Preferably, the reaction is conducted between about 200° C. and about 380° C., most preferably between about 200° C. and about 275° C. Higher temperatures lead to coking of the catalyst. Lower temperatures may allows the reactant alcohols or products to condense on the catalyst bed and cause deactivation of the catalyst.

The reaction typically is carried out at pressures of from about 0.1 atmospheres (10 kPa) to about 5 atmospheres (505 kPa), preferably between about 0.8 atmospheres (81 kPa) to about 1.2 atmospheres (122 kPa), most preferably at ambient pressure. At high pressures hydration of the product may occur. At low pressures operation of the process is made more difficult without providing any added benefit.

The flow of materials through the reactor can vary widely, but must be sufficient to allow the reaction to proceed, and is governed by practical considerations such as convenience, reactor size, and reaction temperature. Typically, the contact time, defined as the reciprocal of the gas hourly space velocity, is from about 0.1 second to about 20 seconds. Preferably, the contact time is from about 0.1 second to about 2 seconds, most preferably from about 0.1 second to about 0.65 second. Short contact times lower dehydration conversion, while longer contact times promote further reactions, such as allylic rearrangement or polymerization.

The preferred halogenated conjugated dienes formed by this process are represented by formula II:

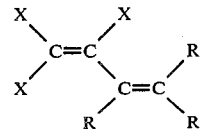

wherein the substituents are as previously described.

The process typically produces conjugated halogenated diene in yields of at least about 70 percent. The tri-halogenated conjugated dienes preferably are produced in yields of at least about 75 percent. More preferably, the yield of trihalogenated conjugated dienes is at least about 80 percent.

The crude product of the reaction can be treated by known methods, such as those described in Example 1, to recover the purified diene.

SPECIFIC EMBODIMENTS

The following examples are intended to illustrate the invention and should not be construed as limiting its scope.

EXAMPLE 1

A quartz glass reactor having the following characteristics is employed:

(a) a preheating zone comprising a 1-inch by 16-inch quartz tube packed with glass balls;

(b) a pump which serves to feed the halogenated unsaturated alcohol into the preheating zone;

(c) a second pump which serves to feed the water into the preheating zone;

(d) a calibrated rotameter which serves to feed an inert carrier gas into the preheating zone, to insure positive head pressure;

(e) a reactor zone comprising a second 1-inch by 16-inch quartz tube, the middle of which contains a ¾-inch by 6-inch bed of dehydration catalyst (Strem 14-7150 silica alumina, 87 percent $SiO_2$, 13 percent $Al_2O_3$, ⅛-inch by ⅛-inch pellets, surface area 410 $m^2/g$, manufactured by Strem Chemicals, Inc.);

(f) a means to connect the preheating zone with the reactor zone;

(g) a condensing means, comprising a 15-inch water-jacketed condenser (kept at 3° C. to 5° C.) and an ice trap, which collects the crude product; and (h) a means for recording and controlling the temperature in the preheating and reactor zones.

1,1,2-Trichloro-3-hydroxy-1-butene (235 g, 1.34 moles at 0.68 g/min) and 378 g of water (at 1.10 g/min) are fed into the preheating zone with an argon flow of 96 ml/min. The preheating zone is maintained at 200° C. and the reactor zone at 250° C. Contact time is 0.415 sec. After it leaves the reactor zone the crude product is collected and the light-yellow organic phase (184 g) is separated from the aqueous phase, is dried over $MgSO_4$, and is distilled to give 1,1,2-trichloro-1,3-butadiene (173 g, 1.10 moles); boiling point 50° C. at 19 mm; boiling point literature 41° C. at 15 mm in 83 percent yield. The diene structure exhibits spectral properties ($^1H$ and $^{13}C$ nuclear magnetic resonance, infrared, mass spectroscopy) consistent with those in the literature.

EXAMPLE 2

The catalyst used in Example 1 is regenerated by heating the reactor to 570° C. and passing air over the bed. The darkened catalyst turns white (the original color) after 8 hours. 1,1,2-Trichloro-3-hydroxy-1-butene (253 g, 1.44 moles) and water are passed through the reactor under conditions as in Example 1. Vapor phase chromatographic analysis of the crude diene fraction indicates a 96 percent conversion of the alcohol. 1,1,2-Trichloro-1,3-butadiene (185 g, 1.1 moles, 35° C./7.3 mm) is obtained in 85 percent yield based on alcohol converted.

EXAMPLE 3

Water (0.80 g/min) and 110 g of an 85:15 isomer mixture of 1,1-dichloro-3-hydroxy-1-butene:1,2-dichloro-3-hydroxy-1-butene (0.78 mole, 0.6 ml/min) are passed through the reactor as described in Example 1, at 240° C. The dried, crude organic phase (80 g) is distilled to give 68 g of a 92:8 isomer mixture of 1,1-dichloro-1,3-butadiene:1,2-dichloro-1,3-butadiene (0.55 mole; boiling point is 35° C. to 43° C. at 77 mm; literature boiling point is 42° C. to 43° C. at 90 mm). The diene structures are in accord with their spectral properties ($^1$H and $^{13}$C nuclear magnetic resonance, intrafred, mass spectroscopy).

EXAMPLES 4-5

The reactor and procedure described in Example 1 are employed to dehydrate 1,1,2-trichloro-3-hydroxy-1-butene with temperature changes as shown in Table I. See Table I for results.

COMPARATIVE EXPERIMENTS 1-5

1,1,2-Trichloro-3-hydroxy-1-butene is dehydrated using a reactor and conditions as described in Example 1, but with catalysts and reaction temperatures as shown in Table I.

TABLE I

Dehydration of 1,1,2-Trichloro-3-hydroxy-1-butene With Various Catalysts (Fixed Bed)[1]

| Run | Catalyst | Temp (°C.) | % Conv[2] | % Yield[3] | % Mass Loss |
|---|---|---|---|---|---|
| C.E.1 | Davison 57 Silica (>99%) | 380 320 | 53 26 | 37 | 30 |
| C.E.2 | Ketchen Alumina 300 m$^2$/g | 340 | 67 | 49 | 30 |
| C.E.3 | Ketchen Alumina 300 m$^2$/g | 325 | 65 | 46 | 31 |
| C.E.4 | 10% WO$_3$ on Alumina 145 m$^2$/g | 265 | 40 | 31 | 23 |
| C.E.5 | Harshaw Titania >99% 135 m$^2$/g | 230 | 39 | — | — |
| Ex.1 | Strem Silica Alumina 87:13 410 m$^2$/g | 250 | 99 | 83 | 8 |
| Ex.4 | Strem Silica Alumina 87:13 410 m$^2$/g | 275 | 100 | 83 | 12 |
| Ex.5 | Strem Silica Alumina 87:13 410 m$^2$/g | 200 | 94 | 77 | 12 |

[1]Typical run using 1 mole alcohol and 35 g catalyst
[2]% Conversion of alcohol
[3]Distilled yield of diene based upon alcohol fed - not consumed
C.E. = Comparative Experiment - not an embodiment of the present invention

What is claimed is:

1. A process comprising contacting, in the presence of steam as a carrier gas, a silica alumina catalyst and at least one alcohol of the formula:

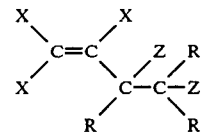

wherein each X is independently hydrogen, chlorine, bromine, or fluorine, with the proviso that no more than one X is hydrogen; one Z is hydrogen and the other Z is hydroxy; and each R is independently hydrogen, alkyl, aralkyl, alkaryl, or aryl; under conditions sufficient to form the corresponding conjugated diene of the formula:

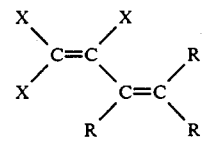

wherein the catalyst comprises 10 to 90 percent silica and 10 to 90 percent alumina, with a surface area of greater than or equal to 350 m$^2$/g.

2. The process of claim 1 wherein the carrier gas is steam and the alcohol/steam mixture is in the vapor phase.

3. The process of claim 2 wherein each R is independently hydrogen or alkyl of from 1 to about 8 carbon atoms.

4. The process of claim 2 wherein the reaction temperature is from about 200° C. to about 275° C.

5. The process of claim 2 wherein greater than about 6 parts by weight of alcohol can be dehydrated per 1 part by weight of catalyst.

6. The process of claim 2 wherein the steam/organic weight ratio is from about 0.5:1 to about 3:1.

7. A process comprising contacting, in the presence of steam as a carrier gas, a silica alumina catalyst and at least one halogenated unsaturated alcohol of the formula:

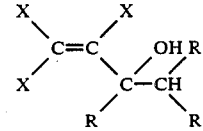

wherein each X is independently chlorine, fluorine, or bromine; and each R is independently hydrogen, alkyl, aralkyl, alkaryl, or aryl; under conditions sufficient to form the corresponding conjugated diene of the formula:

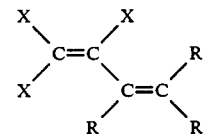

wherein the catalyst comprises 85 to 90 percent silica and 10 to 15 percent alumina, with a surface area of 400 to 450 m$^2$/g.

8. A process comprising contacting, in the presence of steam as a carrier gas, a silica alumina catalyst and at least one halogenated unsaturated alcohol of the formula:

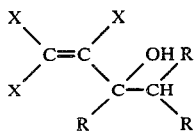

wherein each X is independently chlorine, fluorine, or bromine, and each R is independently hydrogen, alkyl, aralkyl, alkaryl, or aryl; under conditions sufficient to form the corresponding conjugated diene of the formula:

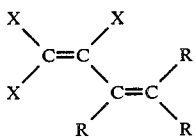

wherein the catalyst comprises 10 to 90 percent silica and 10 to 90 percent alumina, with a surface area of greater than or equal to 350 m$^2$/g.

9. The process of claim 5 wherein each R is independently hydrogen or alkyl of from 1 to about 8 carbon atoms.

10. The process of claim 8 wherein the reaction temperature is from about 150° C. to about 500° C.

11. The process of claim 8 wherein the reaction temperature is from about 200° C. to about 275° C.

12. The process of claim 8 wherein greater than about 6 parts by weight of alcohol can be dehydrated per 1 part by weight of catalyst.

13. The process of claim 8 wherein the steam/organic weight ratio is from about 0.5:1 to about 3:1.

14. The process of claim 8 wherein the yield of the diene is at least about 75 percent.

15. The process of claim 8 wherein the alcohol is 1,1,2-trichloro-3-hydroxy-1-butene.

16. A process comprising contacting, in the presence of a carrier gas, a silica alumina catalyst and at least one alcohol of the formula:

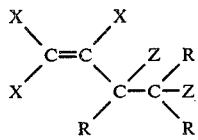

wherein each X is independently hydrogen, chlorine, bromine, or fluorine with the proviso that no more than one X is hydrogen; one Z is hydrogen and the other Z is hydroxy; and each R is independently hydrogen, alkyl, aralkyl, alkaryl, or aryl; under conditions sufficient to form the corresponding conjugated diene of the formula:

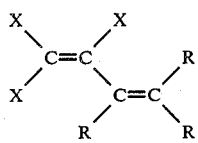

wherein the carrier gas is water and the water/alcohol mixture is in the vapor phase, and wherein the catalyst comprises 85 to 90 percent silica and 10 to 15 percent alumina, with a surface area of greater than or equal to 350 m$^2$/g.

17. The process of claim 16 wherein the catalyst has a surface area of 400 to 450 m$^2$/g.

* * * * *

UNITED STATES PATENT AND TRADEMARK OFFICE
CERTIFICATE OF CORRECTION

PATENT NO. : 4,668,832

DATED : May 26, 1987

INVENTOR(S) : William J. Kruper, Jr.

It is certified that error appears in the above-identified patent and that said Letters Patent is hereby corrected as shown below:

Col. 3, line 48, delete the word "allows" and insert --allow--.

Col. 3, line 68, delete the word "Short" and insert --Shorter--.

Col. 7, Claim 9, line 29, delete "5" and insert --8--.

Signed and Sealed this

Twelfth Day of April, 1988

Attest:

DONALD J. QUIGG

*Attesting Officer*  *Commissioner of Patents and Trademarks*